United States Patent [19]

Ghirardi et al.

[11] Patent Number: 5,166,150

[45] Date of Patent: Nov. 24, 1992

[54] PHARMACEUTICAL COMPOSITIONS COMPRISING 3-AMINO-EPSILON-CAPROLACTAMES FOR ENHANCING THE PROCESS OF LEARNING AND MEMORY

[75] Inventors: Orlando Ghirardi; Roberto Cozzolino; Fabio Giannessi; Domenico Misiti; Maria O. Tinti, all of Rome; Carlo Scolastico, Milan, all of Italy

[73] Assignee: Sigma-Tau Industrie Farmaceutiche Riunite S.p.A., Rome, Italy

[21] Appl. No.: 719,011

[22] Filed: Jun. 21, 1991

[30] Foreign Application Priority Data

Jun. 21, 1990 [IT] Italy .................. 48086 A/90

[51] Int. Cl.$^5$ .............................. A61K 31/55
[52] U.S. Cl. ...................................... 514/212
[58] Field of Search .......................... 514/212

[56] References Cited

PUBLICATIONS

Chem. Abst. 105(1986)–226395f.
Chem. Abst. 108 (1988)–75236p.

Primary Examiner—S. J. Friedman
Attorney, Agent, or Firm—Oblon, Spivak, McClelland, Maier & Neustadt

[57] ABSTRACT

Pharmaceutical compositions for enhancing the process of learning and memory are disclosed, that contain as active principle a 3-amino-ε-caprolactam of formula (1)

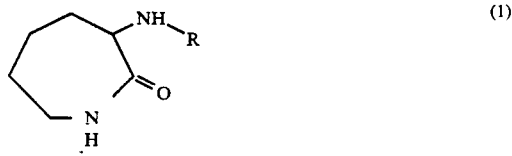

Wherein R is selected from the group consisting of hydrogen, formyl and acetyl.

Orally or parenterally administrable pharmaceutical compositions in unit dosage form comprise from about 100 to about 500 mg of a compound of formula (1).

1 Claim, No Drawings

PHARMACEUTICAL COMPOSITIONS COMPRISING 3-AMINO-EPSILON-CAPROLACTAMES FOR ENHANCING THE PROCESS OF LEARNING AND MEMORY

The present invention relates to orally or parenterally administrable pharmaceutical compositions for enhancing the process of learning and memory comprising as active principle a 3-amino-ε-caprolactam of formula (1)

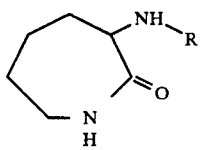
(1)

wherein R is selected from the group consisting of hydrogen, formyl and acetyl.

Disturbances of the processes of learning and memory may become manifest in any patient, regardless of age. These disturbances can be secondary to several pathologies or traumas: alternatively, they can be brought about by the normal process of aging. For this reason, the increase in life expectancy and the attendant increase in number of elderly people have prompted the development of novel methods for treating disorders of learning and memory.

Drugs for treating amnesia, such as piracetam, are already known, (see e.g. Curr. Dev. Psicopharmacol., 3, 22, 1976).

Also the compounds that are taught to be active in accordance with the present invention are known compounds. However, for these compounds no pharmacological activity somehow related to the process of learning and memory has ever been disclosed to date.

In fact, 3-amino-ε-caprolactam is a commercially available product utilized in the production of synthetic fibers and as solvent for high molecular weight polymers (The Merck Index, No. 1762, 11th edition, 1989). 3-formylamino-ε-caprolactam is described as precursor in the production of L-α-amino-ε-caprolactam via the microbiological process disclosed in the Japanese patent JP 63 28 35 91.

Finally, 3-acetylamino-ε-caprolactam is disclosed as component of liquid detergents in the Japanese patent JP 58 37 097 and as reaction intermediate by ADAMCZESKI et al., J. Am. Chem. Soc. 1989, 111, 647–654.

As shown hereinbelow, the above-identified compounds that are the active ingredients of the pharmaceutical compositions of the present invention are potent enhancers of the process of learning and memory. These compounds are more potent than piracetam.

Since the compounds contain a chiral carbon atom, they can exist as two enantiomers designated (R) and (S). It has been found that both enantiomers are pharmacologically active.

Although, as previously indicated, the compounds of formula (1) are known compounds, examples of preparation of those that are less easily available on the market are given below.

EXAMPLE 1

Preparation of (S)-3-acetylamino-ε-caprolactam (ST 755).

Triethylamine (1.91 g; 18.88 mmoles) was added to (S)-3-amino-ε-caprolactam (2.2 g; 17.16 mmoles) in $CH_2Cl_2$ (50 mL). To the resulting solution acetylchloride (1.35 g; 17.16 mmoles) in $CH_2Cl_2$ (10 mL) was added under stirring. The solution was kept under stirring at room temperature overnight. To the solution $Et_2O$ was then added under stirring. The solid that formed was filtered off and the filtrate was brought to dryness and chromatographed over silica gel using EtOAc as eluant. 1.8 g of the product were obtained.

Yield = 62%.

M.P. = 147°–149° C.

TLC on silica gel; eluant: EtOAc-MeOH 8:2. $R_F = 0.47$ $[\alpha]_D^{25} = +13.7°$ MeOH (C=1)

Elementary analysis for $C_8H_{14}N_2O_2$: Calculated: C56.45, H8.29, N16.45. Found: C56.78, H8.58, N16.29.

$^1$HNMR($CDCl_3$):

δ7.2–7(br,2H,—NHCOCHNHCO),4.6–4.5(m,1H,—CHNCO—)3.4–3.2(m,2H,—CH$_2$CH$_2$NCO—),2.15–1.75(m,7H,—CH$_2$CH$_2$CH$_2$CH-NCOCH$_3$),1.60–1.3(m,2H,—CH$_2$CH$_2$CHNCO—)

HPLC

μ Bondapack $C_{18}$. Length = 300 mm. Inner diameter = 3.9 mm. Size = 10 μm.

Eluant = $KH_2PO_2$ 0.05/$CH_3CN$ (80:20).

Flow rate = 1 mL/min.

Retention time = 3.77 min.

EXAMPLE 2

Preparation of (S)-3-(formylamino)-ε-caprolactam (ST 797).

CDI (4.55 g; 28.08 mmoles) was added to formic acid (1.08 g; 23.40 mmoles) in $CH_2Cl_2$(60 mL). The resulting solution was kept under stirring for 30 minutes and (S)-3-amino-ε-caprolactam (3 g; 23.40 mmoles) was added thereto.

After 24 hours, $Et_2O$ was added under stirring to the resulting mixture. The precipitate (2.6 g) that formed was collected by filtration and purified by crystallization from $CHCl_3/Et_2O$ furnishing 1.75 g of compound.

Yield = 48% (calculated on the crystallized product).

$[\alpha]_D^{25} = +83°$ $CHCl_3$ (C=1)

M.P. = 176° C.

TLC on silica gel; eluant EtOAc. $R_F = 0.1$.

Elementary analysis for $C_7H_{12}N_2O_2$: Calculated: C53.83, H7.74, N17.93. Found: C54.35, H7.62, N17.55.

$^1$HNMR(DMSO-d$_6$): δ8.25(br,1H,—HN—CHO),8.1(s,1H,—CHO),7.9(br,1H,HNCO—), 4.6–4.45(m,1H,—CHNCO—),3.35–3.05(m,2H,—CH$_2$NCO—),2–1.60(m,4H,—CH$_2$CH$_2$CH$_2$CHN—),1.55–1.10(m,2H,—CH$_2$CH$_2$CH$_2$CHN—).

HPLC

μ Bondapack $C_{18}$. Length = 300 mm. Inner diameter = 3.9 mm. size = 10 μm.

Eluant = $KH_2PO_4$ 0.05M/$CH_3CN$ (70:30).

Flow rate = 1 mL/min.

Retention time = 4.81 min.

The activity of the compounds of the invention was assessed in several pharmacological tests. Some of these tests wherein piracetam was used as reference standard are illustrated hereinbelow.

(A) Assessment of the Antiamnesic Activity

In order to assess the antiamnesic activity the passive avoidance test in mice was used. Amnesia was brought about by administration of scopolamine (cfr. Bammer, Pharmacological investigations of neurotransmitter involvement in passive avoidance responding: a review and some new results. *Neurosci. Biobehav. Rev.*, 6(3) 247-296, 1982); or by electroconvulsive shock (ECS) (cfr. Bammer et al., A screening method for substances potentially active on learning and memory. *J. Pharmacol. Methods* Vol.: 8(4) 255-263, 1982).

Male CDI mice (Charles River—Italy) wheighing 25-26 g were used for the scopolamine-induced amnesia test.

Male CDI mice (Charles River—Germany) fed on a normal diet, were used for the ECS-induced amnesia test.

The compounds were administered i.p.; 0.9 mg/kg in the scopolamine-induced amnesia test; and 9 and 0.9 mg/kg in the ECS-induced amnesia test. All doses were equimolar to piracetam.

The compounds were dissolved in saline.

The apparatus for passive avoidance conditioning was a black plastic chamber (42×42 cm, height 40 cm) provided with a floor constructed of métal rods that could be electrified. From the front wall extended a white runway, 30 cm long and 10 cm wide provided with side walls 12 cm high, which led into the box through a guillotine door. The runway was lightened by a 60 W lamp (cfr. Ader et al., Retention of passive avoidance response as a function of the intensity and duration of electric shock. *Psychon. Sci.*, 26(3), 125-127, 1972).

Passive Avoidance Following Scopolamine-Induced Amnesia

The animals were administered the compounds and scopolamine (1.5 mg/kg s.c.) 30 minutes and 15 minutes, respectively, before the test and were then placed on the runway. After one minute of adaptation, the door was raised and the time employed by the animal to enter the darkened box with all four feet, was recorded.

Upon entry, the guillotine door was lowered and three seconds thereafter the rods were electrified, 0.21 mA for 2 seconds.

Immediately thereafter the animal was placed in the housing cage. Retention was assessed 24 hours later by placing the animal on the runway and again evaluating the latency in entering the chamber, using an endpoint of 300 s (cfr. Bammer, loc. cit.).

In each experiment, two groups of animals in addition to the treated ones were used, that were defined as follows:

(1) ceiling control animals (treated with placebo and not subjected to amnesia treatment with scopolamine or ECS) to ensure that these animals not treated with the amnesia agent remembered the task;

(2) base-line control animals (treated with placebo and subjected to amnesia treatment with scopolamine or ECS) to ensure that ECS or scopolamine produced amnesia in the animals not treated with the compounds of the present invention.

The results of each compound under examination were expressed as percentage of amnesia reversal (AR) in order to make comparisons across the tested compounds.

AR is defined as follows:

$$AR = \frac{CI_t}{CI_c} \cdot 100$$

wherein CI, comparison index (the subscripts "t" and "c" refer to "treated" and "ceiling control", respectively) is defined by the formula $$CI = [\Sigma Aij/Ni.Nj)]100$$

wherein

Ni is the number of animals belonging to the i-nth group (ceiling control or treated animals);

Nj is the number of animals belonging to the j-nth group (base-line control animals), and Aij is a binary function that can take only the values +1, 0 or −1 depending on whether the latency time (in seconds) of an animal belonging to the i-nth group, Xi, is higher than, the same as or smaller than the latency time (in seconds) of an animal of the j-nth group, Xj.

The sum $\Sigma Aij$ encompasses all the possible pairs obtained by combining each term Xi with each term Xj.

Whenever in performing the test the comparison index (CI) between ceiling control animals and base-line control animals, generally expected to range between 60 and 80%, turned out to be lower than 40%, the data for the whole experiment were discarded.

The results are shown in Table 1.

TABLE 1

Passive avoidance following scopolamine-induced amnesia. The Table shows the ARs of some compounds of the present invention. The number of animals (n.) and the AR of each compound are reported.

|  | 0.9 mg n° | $kg^{-1}$ % AR |
|---|---|---|
| Animals in the ceiling control group | 356 | 100 |
| Animals in the base-line control group | 625 | 0 |
| PIRACETAM | 10 | 19 |
| ST 755 | 22 | 41 |
| ST 797 | 24 | 49 |
| ST 781* | 23 | 50 |
| ST 818* | 23 | 47 |

*The compound designated ST 781 is (S)-3-amino-ε-caprolactam; ST 818 is the (R) enantiomer of ST 781.

Passive Avoidance Following ECS-Induced Amnesia 0.30 minutes following treatment with the compounds, the animals were placed on the runway. After one minute of adaptation, the door was raised and the time employed by the animal to enter the darkened box with all four feet, was recorded.

Upon entry, the guillotine door was lowered and three seconds thereafter the rods were electrified, 0.24 mA for 2 seconds.

The mouse was then removed from the chamber and immediately administered an electroshock delivered through spring clips attached to the ears (square wave, intensity 20 mA, amplitude 0.6 msec. duration 0.5 s. frequency 50 Hz).

Retention was assessed 24 hours later by placing the animal on the runway and again evaluating the latency in entering the chamber, using an end-point of 300 seconds (Bammer, loc. cit.). In each experiment, two groups of animals (a ceiling control group and a baseline control group) in addition to the treated animals were used, as previously described.

The results for each compound under examination were expressed as amnesia reversal (AR) in such a way as to make comparisons across the tested compounds. Amnesia reversal was assessed by using the comparison index (CI), calculated according to the formula previously given.

The results obtained are shown in Table 2.

TABLE 2

Passive avoidance following ECS-induced amnesia. The table shows the ARs of some compounds of the present invention. The number of animals (n.) and AR of each tested compound at various dose levels are reported.

|  | 9 mg kg$^{-1}$ | | 0.9 mg kg$^{-1}$ | |
| --- | --- | --- | --- | --- |
|  | n° | AR | n° | AR |
| Ceiling control group | 540 | 100 | 547 | 100 |
| Base-line control group | 1018 | 0 | 1030 | 0 |
| PIRACETAM | 30 | 0 | 27 | 0 |
| ST 755 | 11 | 14 | 12 | 7 |
| ST 797 | 12 | 55 | 24 | 71 |
| ST 781* | 24 | 26 | 23 | 37 |
| ST 818* | 24 | 25 | 36 | 0 |

*The compound designated ST 781 is (S)-3-amino-ε-caprolactam; ST 818 is the (R) enantiomer of ST 781.

(B) Behavioural profile

The behavioural profile was assessed in male CD1 mice (Charles River, Italy) weighing 22-24 g, using the Irwin test (IRWIN S., Drug screening and evaluation procedures 136, 123-128, 1962). The animals had been caged under normal conditions and kept fasting for the last 18 hours. Following administration of the compounds, the behaviour of the animals was monitored for 6 hours.

The compounds were suspended in 10% arabic gum and orally administered at doses equimolar to 90, 23, 5.4 and 1.4 mg piracetam/10 mL/kg of body weight.

The animals of the control groups were administered 10% arabic gum (10 mL/kg, orally).

No compound altered, at the tested doses, the behavioural profile.

(C) Analgesic Activity

The analgesic activity was assessed in CD1 mice (Charles River, Italy) weighing 22-24 g, utilizing the hot plate test (56° C.).

The animals, kept under normal caging conditions and kept fasting for 18 hours, were placed on the hot plate for 30, 60, 120 and 180 minutes following the administration of 90, 23, 5.4 and 1.4 mg/10 mL/kg of each compound under examination.

The analgesic activity was assessed by measuring the increase (in seconds) of the time the animals continued to stay on the hot plate. None of the tested compounds was shown to possess analgesic activity.

The compounds of the present invention can be formulated into orally or parenterally administrable pharmaceutical compositions. Suitable excipient and compositions for tablets, vials and the like are illustrated in the Canadian patent 1.100.515.

Pharmaceutical compositions in unit dosage form comprise between about 100 and about 500 mg of active ingredient.

We claim:

1. A method for enhancing the processes of learning and memory in a subject in need of such enhancement which comprises administering to said subject an effective amount of a 3-amino-ε-caprolactam of formula (1)

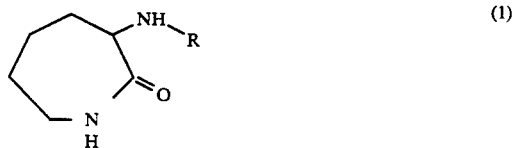

(1)

wherein R is selected from the group consisting of hydrogen, formyl and acetyl.

* * * * *